(12) United States Patent
Nishino et al.

(10) Patent No.: US 7,300,953 B2
(45) Date of Patent: Nov. 27, 2007

(54) PROCESS FOR PREPARING NITRILE COMPOUND, CARBOXYLIC ACID COMPOUND OR CARBOXYLIC ACID ESTER COMPOUND

(75) Inventors: Shigeyoshi Nishino, Ube (JP); Kenji Hirotsu, Ube (JP); Hidetaka Shima, Ube (JP); Keiji Iwamoto, Ube (JP); Takashi Harada, Ube (JP)

(73) Assignee: Ube Industries, Ltd, Ube-shi (JP)

( * ) Notice: Subject to any disclaimer, the term of this patent is extended or adjusted under 35 U.S.C. 154(b) by 0 days.

(21) Appl. No.: 10/572,373

(22) PCT Filed: Sep. 17, 2004

(86) PCT No.: PCT/JP2004/013626

§ 371 (c)(1),
(2), (4) Date: Mar. 16, 2006

(87) PCT Pub. No.: WO2005/028410

PCT Pub. Date: Mar. 31, 2005

(65) Prior Publication Data

US 2006/0287541 A1     Dec. 21, 2006

(30) Foreign Application Priority Data

Sep. 19, 2003 (JP) .............................. 2003-328515
Sep. 19, 2003 (JP) .............................. 2003-328516
Apr. 15, 2004 (JP) .............................. 2004-120502
May 13, 2004 (JP) .............................. 2004-143637

(51) Int. Cl.
*A61K 31/075* (2006.01)
*C07D 309/08* (2006.01)

(52) U.S. Cl. ...................... 514/451; 549/426
(58) Field of Classification Search ................ 514/451; 549/426
See application file for complete search history.

(56) References Cited

FOREIGN PATENT DOCUMENTS

| EP | 0 659 181 B1 | 6/1995 |
|---|---|---|
| JP | 54-122220 A | 9/1979 |
| JP | 59-51251 A | 3/1984 |
| JP | 8-501299 A | 2/1996 |
| JP | 2000281672 A * | 10/2000 |
| WO | WO-94/05639 A1 | 3/1994 |

OTHER PUBLICATIONS

Lawerence I. Kruse et al., J. Med. Chem. 1990, vol. 33, No. 2, pp. 781 to 789.
Christoph Strassier et al., Helvetica Chimica Acta, vol. 80, pp. 1528 to 1554, 1997.

* cited by examiner

*Primary Examiner*—Kamal A. Saeed
*Assistant Examiner*—Shawquia Young
(74) *Attorney, Agent, or Firm*—Birch, Stewart, Kolasch & Birch, LLP

(57) ABSTRACT

The present invention discloses a process for preparing a nitrile compound, a carboxylic acid compound or a carboxylic acid ester compound represented by the formula (2):

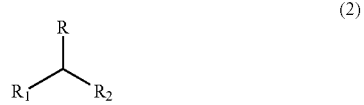

wherein R represents a cyano group, a carboxyl group or an ester group, $R^1$ and $R^2$ each represent a group which does not participate in the reaction, which may have a substituent, and $R^1$ and $R^2$ may be combined to each other to form a ring, which comprises subjecting an acetic acid compound represented by the formula (1):

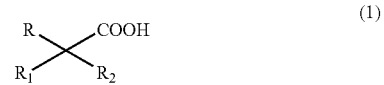

wherein R, $R^1$ and $R^2$ have the same meanings as defined above,
to decarboxylation in the presence of a metal catalyst.

5 Claims, No Drawings

PROCESS FOR PREPARING NITRILE COMPOUND, CARBOXYLIC ACID COMPOUND OR CARBOXYLIC ACID ESTER COMPOUND

TECHNICAL FIELD

The present invention relates to a process for preparing a nitrile compound, a carboxylic acid compound or a carboxylic acid ester compound from an acetic acid compound. The present invention also relates to a process for preparing a 4-substituted tetrahydropyran from a 4-substituted tetrahydropyran-4-carboxylic acid or a bis(2-halogenoethyl)ether and a 2-substituted acetic acid ester. The present invention further relates to a process for preparing a 4-aminomethyltetrahydropyran and an acid salt thereof from a 4-cyanotetrahydropyran. The nitrile compound, the carboxylic acid compound or the carboxylic acid ester compound, the 4-substituted tetrahydropyran (4-cyanotetrahydropyran, tetrahydropyran-4-carboxylic acid) and the 4-aminomethyltetrahydropyran and an acid salt thereof are useful compounds as a starting material or a synthetic intermediate of medicines, agricultural chemicals, etc.

BACKGROUND ART

Heretofore, as a method for preparing a nitrile compound, a carboxylic acid compound or a carboxylic acid ester compound from an acetic acid compound, it has been known, for example, a method in which acetonitrile is obtained by heating cyanoacetic acid to 160° C. or higher (for example, see Chem. Ber., 7, 1382 (1874)) or a method in which acetic acid is obtained by heating malonic acid in p-azoxyanisole at 141° C. (for example, see J. Indian Chem. Soc.,58, 868 (1981)). However, in either of the above-mentioned methods, high reaction temperatures are required, and yields are low or there is no description about yields, etc., so that these methods are not satisfied as an industrial process for preparing a nitrile compound, a carboxylic acid compound or a carboxylic acid ester compound.

Also, as a method for preparing 4-substituted tetrahydropyran from 4-substituted tetrahydropyran-4-carboxylic acid, or from bis(2-halogenoethyl)ether and 2-substituted acetic acid ester, it has been known a method, for example, in which bis(2-chloroethyl)ether and ethyl cyanoacetate are reacted to prepare ethyl 4-cyanotetrahydropyran-4-carboxylate, then the resulting material is hydrolyzed to prepare 4-cyanotetrahydropyran-4-carboxylic acid, and further, it is heated at 180 to 200° C. to produce 4-cyanotetrahydropyran with overall yield of 12.2% (for example, see J. Chem. Soc., 1930, 2525). Also, it has been known a method in which bis(2-chloroethyl)ether and diethyl malonate are reacted to prepare diethyl tetrahydropyran-4,4-dicarboxylate, then, the resulting material is hydrolyzed to prepare tetrahydropyran-4,4-dicarboxylic acid, and then, the resulting material is heated to 180° C. to prepare tetrahydropyran-4-carboxylic acid with overall yield of 31.8% (for example, see Helv. Chim. Acta., 80, 1528 (1997)). However, in either of the above-mentioned methods, high reaction temperatures are required, and yields are low, so that these methods are not satisfied as an industrial process for preparing 4-substituted tetrahydropyran.

Moreover, as a method for preparing 4-aminomethyl-tetrahydropyran and an acid salt thereof from 4-cyanotetrahydropyran, it has been known a method, for example, in which 4-cyanotetrahydropyran and hydrogen are reacted in the presence of Raney nickel in anhydrous ethanol (for example, see International Patent Publication No. 94/05639). However, according to this method, yield of the objective product, 4-aminomethyltetrahydropyran, is low, and a large amount of a by-product (bis(4-tetrahydropyranylmethyl)amine) is produced, etc., so that this is not satisfied as an industrial process for preparing 4-aminomethyltetrahydropyran and an acid salt thereof.

DISCLOSURE OF THE INVENTION

An object of the present invention is to solve the above-mentioned problems and to provide an industrially suitable process for preparing a nitrile compound, a carboxylic acid compound or a carboxylic acid ester compound in which a nitrile compound, a carboxylic acid compound or a carboxylic acid ester compound, in particular, 4-substituted tetrahydropyran can be prepared from an acetic acid compound, in particular, 4-substituted tetrahydropyran-4-carboxylic acid or bis(2-halogenoethyl)ether and 2-substituted acetic acid ester under mild conditions with a simple and easy process and with high yield.

Another object of the present invention is to solve the above-mentioned problems and to provide an industrially suitable process for preparing 4-aminomethyltetrahydropyran and an acid salt thereof in which 4-aminomethyltetrahydropyran and an acid salt thereof can be prepared from 4-cyanotetrahydropyran with high yield.

The first embodiment of the present invention relates to a process for preparing a nitrile compound, a carboxylic acid compound or a carboxylic acid ester compound represented by the formula (2):

wherein R represents a cyano group, a carboxyl group or an ester group, $R^1$ and $R^2$ each represent a group which does not participate in the reaction, each of which may have a substituent(s), and $R^1$ and $R^2$ may form a ring by binding to each other, which comprises subjecting an acetic acid compound represented by the formula (1):

wherein R, $R^1$ and $R^2$ have the same meanings as defined above, to decarboxylation in the presence of a metal catalyst.

The second embodiment of the present invention relates to a process for preparing a 4-substituted tetrahydropyran represented by the formula (4):

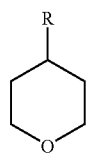
(4)

wherein R has the same meaning as defined above, which comprises subjecting a 4-substituted tetrahydropyran-4-carboxylic acid represented by the formula (3):

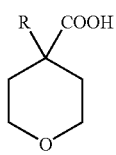
(3)

wherein R has the same meaning as defined above, to decarboxylation in the presence of a metal catalyst.

The third embodiment of the present invention relates to a process for preparing a 4-substituted tetrahydropyran which comprises the steps of (A) a cyclization step in which bis(2-halogenoethyl)ether represented by the formula (5):

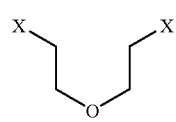
(5)

wherein X represents a halogen atom, and a 2-substituted acetic acid ester represented by the formula (6):

(6)

wherein $R^3$ represents a hydrocarbon group, and R has the same meaning as defined above, are reacted in the presence of a base in an organic solvent to prepare a mixture of a 4-substituted tetrahydropyran-4-carboxylic acid ester represented by the formula (7):

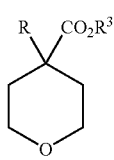
(7)

wherein R and $R^3$ have the same meanings as defined above, and a 4-substituted tetrahydropyran-4-carboxylic acid represented by the formula (3):

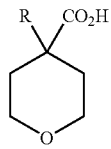
(3)

wherein R has the same meaning as defined above, (B) then, a hydrolysis step in which the above-mentioned mixture is hydrolyzed to prepare a 4-substituted tetrahydropyran-4-carboxylic acid represented by the formula (3):

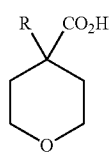
(3)

wherein R has the same meaning as defined above, (C) further, a decarboxylation step in which the 4-substituted tetrahydropyran-4-carboxylic acid is subjected to decarboxylation in the presence of a metal catalyst to prepare a 4-substituted tetrahydropyran represented by the formula (4):

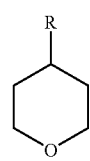
(4)

wherein R has the same meaning as defined above.

The fourth embodiment of the present invention relates to a process for preparing a 4-aminomethyltetrahydropyran represented by the formula (9):

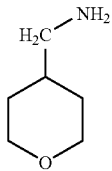
(9)

and an acid salt thereof which comprises reacting a 4-cyanotetrahydropyran represented by the formula (8):

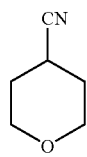

(8)

which is a compound in which R is a cyano group in the above-mentioned formula (4) with hydrogen in the presence of Raney nickel in a solvent containing ammonia.

BEST MODE FOR CARRYING OUT THE INVENTION

The acetic acid compound or the 4-substituted tetrahydropyran-4-carboxylic acid to be used in the decarboxylation in the first and the second embodiments of the present invention is represented by the above-mentioned formula (1) or (3). In the formula (1) or (3), R represents a cyano group, a carboxyl group or an ester group. As the ester group, it is not specifically limited so long as it is a group which forms an ester with a carboxyl group, and there may be mentioned, for example, a carboxyalkyl ester group, a carboxyaralkyl ester group, a carboxyaryl ester group, a carboxycycloalkyl ester group, etc. As the carboxyalkyl ester group, there may be mentioned those to which a linear or branched alkyl group having 1 to 6 carbon atoms is bonded, more specifically, a carboxymethyl ester group, a carboxyethyl ester group, a carboxy-n-propyl ester group, a carboxyisopropyl ester group, a carboxy-n-butyl ester group, a carboxyisobutyl ester group, a carboxy-t-butyl ester group, etc. As the carboxyaralkyl ester group, there may be mentioned a group in which a linear or branched alkyl group having 1 to 3 carbon atoms bound to an aryl group, more specifically, a carboxybenzyl ester group, a carboxyphenethyl ester group, a carboxyphenylpropyl ester group, etc. As the carboxyaryl ester group, there may be mentioned a group in which an aryl group having 6 to 20 carbon atoms bound, more specifically, a carboxyphenyl ester group, a carboxytolyl ester group, a carboxyxylyl ester group, a carboxymesityl ester group, a carboxynaphthyl ester group, etc. As the carboxycycloalkyl ester group, there may be mentioned a group in which a cycloalkyl group having 3 to 6 carbon atoms bound, more specifically, a carboxycyclopropyl ester group, a carboxycyclobutyl ester group, a carboxycyclopentyl ester group, a carboxycyclohexyl ester group, etc. Of these, preferred is a carboxyalkyl ester group, more preferred is a carboxymethyl ester group or a carboxyethyl ester group.

Also, $R^1$ and $R^2$ in the formula (1) each represent a group which does not participate in the reaction, which may have a substituent(s), more specifically, for example, a hydrogen atom, an alkyl group, a cycloalkyl group, an aralkyl group, an aryl group, a halogen atom, a hydroxyl group, an alkoxyl group, an alkylthio group, a nitro group, a cyano group, a carbonyl group or an amino group. Incidentally, $R^1$ and $R^2$ may form a ring by binding to each other. Specific examples of the compound in which a ring is formed, there may be exemplified by a 4-substituted tetrahydropyran-4-carboxylic acid represented by the the above-mentioned formula (3) in which $R^1$ and $R^2$ form a ring through an oxygen atom in the second embodiment of the present invention as a particularly preferred compound.

As the above-mentioned alkyl group, there may be mentioned, for example, a linear or branched alkyl group having 1 to 10 carbon atoms, more specifically, a methyl group, an ethyl group, a propyl group, a butyl group, a pentyl group, a hexyl group, a heptyl group, an octyl group, a nonyl group, a decyl group, etc. are mentioned. Incidentally, these groups contain various kinds of isomers.

As the above-mentioned cycloalkyl group, there may be mentioned, for example, a cycloalkyl group having 3 to 10 carbon atoms, more specifically, a cyclopropyl group, a cyclobutyl group, a cyclopentyl group, a cyclohexyl group, a cycloheptyl group, a cyclooctyl group, etc. are mentioned.

As the above-mentioned aralkyl group, there may be mentioned, for example, an aryl group bonded to a linear or branched alkyl group having 1 to 3 carbon atoms, more specifically, a benzyl group, a phenethyl group, a phenylpropyl group, etc. are mentioned. Incidentally, these groups contain various kinds of isomers.

As the above-mentioned aryl group, there may be mentioned, for example, an aryl group having 6 to 20 carbon atoms, more specifically, a phenyl group, a p-tolyl group, a naphthyl group, an anthryl group, etc. Incidentally, these groups contain various kinds of isomers.

As the above-mentioned halogen atom, there may be mentioned, for example, a fluorine atom, a chlorine atom, a bromine atom, and an iodine atom.

As the above-mentioned alkoxyl group, there may be mentioned, for example, a linear or branched alkoxyl group having 1 to 6 carbon atoms, more specifically, a methoxyl group, an ethoxyl group, a propoxyl group, etc. Incidentally, these groups contain various kinds of isomers.

As the above-mentioned alkylthio group, there may be mentioned, for example, a linear or branched alkylthio group having 1 to 10 carbon atoms, more specifically, a methylthio group, an ethylthio group, a propylthio group, etc. Incidentally, these groups contain various kinds of isomers.

The above-mentioned alkyl group, cycloalkyl group, aralkyl group, aryl group, alkoxyl group, alkylthio group or amino group may have a substituent(s). As the substituent(s), there may be mentioned a substituent(s) formed through a carbon atom, a substituent(s) formed through an oxygen atom, a substituent(s) formed through a nitrogen atom, a substituent(s) formed through a sulfur atom, a halogen atom, etc.

As the above-mentioned substituent formed through a carbon atom, there may be mentioned, for example, a linear or branched alkyl group having 1 to 10 carbon atoms such as a methyl group, an ethyl group, a propyl group, a butyl group, a pentyl group, a hexyl group, etc.; a cycloalkyl group having 3 to 10 carbon atoms such as a cyclopropyl group, a cyclobutyl group, a cyclopentyl group, a cyclohexyl group, etc.; an alkenyl group having 2 to 10 carbon atoms such as a vinyl group, an allyl group, a propenyl group, a cyclopropenyl group, a cyclobutenyl group, a cyclopentenyl group, etc.; a heterocyclic group such as a pyrrolidyl group, a pyrrolyl group, a furyl group, a thienyl group, etc.; an aryl group having 6 to 20 carbon atoms such as a phenyl group, a tolyl group, a xylyl group, a biphenylyl group, a naphthyl group, an anthryl group, a phenanthryl group, etc.; an acyl group (which may be converted into acetal) having 1 to 10 carbon atoms such as a formyl group, an acetyl group, a propionyl group, an acryloyl group, a pivaloyl group, a cyclohexylcarbonyl group, a benzoyl group, a naphthoyl group, a toluoyl group, etc.; an alkoxycarbonyl group having 2 to 10 carbon atoms such as a methoxycarbonyl group, an ethoxycarbonyl group, etc.; an aryloxycarbonyl group having 7 to 20 carbon atoms such as a phenoxycarbonyl group, etc.; a halogenated alkyl group having 1 to 10 carbon atoms such as a trifluoromethyl group, etc.; a cyano group, etc. Incidentally, these groups contain various kinds of isomers.

As the above-mentioned substituent formed through a oxygen atom, there may be mentioned, for example, a hydroxyl group; an alkoxyl group having 1 to 10 carbon atoms such as a methoxyl group, an ethoxyl group, a propoxyl group, a butoxyl group, a pentyloxyl group, a hexyloxyl group, a heptyloxyl group, a benzyloxyl group, a piperidyloxyl group, a pyranyloxyl group, etc.; an aryloxyl group having 6 to 20 carbon atoms such as a phenoxyl group, a tolyloxyl group, a naphtyloxyl group, etc. Incidentally, these groups contain various kinds of isomers.

As the above-mentioned substituent formed through a nitrogen atom, there may be mentioned, for example, a primary amino group such as a methylamino group, an ethylamino group, a butylamino group, a cyclohexylamino group, a phenylamino group, a naphthylamino group, etc.; a secondary amino group such as a dimethylamino group, a diethylamino group, a dibutylamino group, a methylethylamino group, a methylbutylamino group, a diphenylamino group, etc.; a heterocyclic amino group such as a morpholino group, a thiomorpholino group, a piperidino group, a piperazinyl group, a pyrazolidinyl group, a pyrrolidino group, an indolyl group, etc.; an imino group, etc. Incidentally, these groups contain various kinds of isomers.

As the above-mentioned substituent formed through a sulfur atom, there may be mentioned, for example, a mercapto group; a thioalkoxyl group having 1 to 6 carbon atoms such as a thiomethoxyl group, a thioethoxyl group, a thiopropoxyl group, etc.; a thioaryloxyl group having 6 to 20 carbon atoms such as a thiophenoxyl group, a thiotolyloxyl group, a thionaphtyloxyl group, etc. Incidentally, these groups contain various kinds of isomers.

As the above-mentioned a halogen atom, there may be mentioned a fluorine atom, a chlorine atom, a bromine atom, and an iodine atom.

As the specific examples of the acetic acid compound represented by the formula (1) in the first embodiment of the present invention, there may be mentioned, for example, cyanoacetic acid, malonic acid, 2-methylcyanoacetic acid, 2,2-dimethylcyanoacetic acid, malonic acid monomethyl ester, 2-methyl malonic acid, 2,2-dimethyl malonic acid, etc.

Specific examples of the 4-substituted tetrahydropyran-4-carboxylic acid represented by the formula (3) in the second embodiment of the present invention may be mentioned 4-cyanotetrahydropyran-4-carboxylic acid, tetrahydropyran-4,4-dicarboxylic acid, tetrahydropyran-4,4-dicarboxylic acid monomethyl ester, tetrahydropyran-4,4-dicarboxylic acid monoethyl ester, tetrahydropyran-4,4-dicarboxylic acid mono-n-propyl ester, tetrahydropyran-4,4-dicarboxylic acid mono-isopropyl ester, tetrahydropyran-4,4-dicarboxylic acid mono-n-butyl ester, tetrahydropyran-4,4-dicarboxylic acid mono-isobutyl ester, tetrahydropyran-4,4-dicarboxylic acid mono-tert-butyl ester, tetrahydropyran-4,4-dicarboxylic acid monocyclopropyl ester, tetrahydropyran-4,4-dicarboxylic acid monobenzyl ester, tetrahydropyran-4,4-dicarboxylic acid monophenyl ester, etc.

As the metal catalyst to be used in the decarboxylation of the present invention is at least one catalyst of a metal selected from the group consisting of copper, iron, nickel and zinc, more specifically, there may be mentioned for example, a copper catalyst such as copper powder, copper(I) oxide, copper(II) oxide, copper(I) chloride, copper(II) chloride, copper(I) bromide, copper(II) bromide, etc.; an iron catalyst such as iron, iron(II) oxide, iron(III) oxide, iron(II) chloride, iron(III) chloride, iron(II) bromide, iron(III) bromide, etc.; a nickel catalyst such as nickel(II) oxide, nickel (III) oxide, nickel(II) chloride, nickel(II) bromide, nickel(II) acetylacetonate, Raney nickel, etc.; a zinc catalyst such as zinc powder, zinc chloride, zinc bromide, etc., preferably copper powder, copper(I) oxide, iron, nickel(II) acetylacetonate, zinc powder, more preferably copper powder, copper(I) oxide, particularly preferably copper(I) oxide is used. Incidentally, these metal catalysts may be used alone or in combination of two or more kinds.

An amount of the above-mentioned metal catalyst to be used is preferably 0.001 to 10 mols, more preferably 0.001 to 1.0 mol, particularly preferably 0.01 to 0.5 mol in terms of a metal atom based on 1 mol of the acetic acid compound or the 4-substituted tetrahydropyran-4-carboxylic acid.

The decarboxylation of the present invention is preferably carried out in a solvent. As the solvent to be used, it is not specifically limited so long as it does not inhibit the reaction, and there may be used, for example, water; a secondary amine such as dibutylamine, piperidine, 2-pipecoline, etc.; a tertiary amine such as triethylamine, tributylamine, etc.; a pyridine such as pyridine, methylpyridine, dimethylaminopyridine, etc.; a quinoline such as quinoline, isoquinoline, methylquinoline, etc.; an amide such as N,N-dimethylformamide, N,N-dimethylacetamide, N-methylpyrrolidone, etc.; a urea such as N,N'-dimethylimidazolidinone, etc.; a sulfoxide such as dimethyl sulfoxide, sulfolane, etc.; an alcohol such as n-propyl alcohol, n-butyl alcohol, etc.; an ether such as diisopropylether, dioxane, cyclopropylmethylether, etc.; an aromatic hydrocarbon such as toluene, xylene, etc.; an acetic acid ester such as ethyl acetate, butyl acetate, etc., preferably a tertiary amine, a pyridine, an amide, a sulfoxide, or a mixed solvent thereof with an aromatic hydrocarbon or an acetic acid ester, more preferably triethylamine, pyridine, N,N-dimethylformamide, N,N-dimethylacetamide, N-methylpyrrolidone, N,N'-dimethylimidazolidinone, dimethyl sulfoxide, or a mixed solvent thereof with toluene, ethyl acetate or butyl acetate. Incidentally, these organic solvents may be used alone or in combination of two or more in admixture.

An amount of the above-mentioned solvent to be used may be optionally adjusted depending on a degree of uniformity or condition of stirring of the reaction mixture, and is preferably 0.1 to 100 ml, more preferably 0.5 to 50 ml, particularly preferably 1 to 10 ml based on 1 g of the acetic acid compound or the 4-substituted tetrahydropyran-4-carboxylic acid.

The decarboxylation of the present invention can be carried out, for example, by a method in which an acetic acid compound, a metal catalyst and a solvent are mixed, and reacted under stirring, etc. A reaction temperature at that time is preferably 50 to 150° C., more preferably 80 to 130° C., and a reaction pressure is not specifically limited.

Incidentally, the nitrile compound or the carboxylic acid compound represented by the formula (2) or the 4-substituted tetrahydropyran represented by the formula (4) which are final products can be isolated and purified by a general method, for example, filtration, concentration, distillation, recrystallization, column chromatography, etc., after completion of the reaction.

As the specific examples of the nitrile compound, carboxylic acid compound or carboxylic acid ester compound represented by the formula (2) obtained in the first embodiment of the present invention, there may be mentioned, for example, acetonitrile, propionitrile, isobutyronitrile, methyl acetate, acetic acid, propionic acid, 2-methylpropionic acid, etc.

As the specific examples of the 4-substituted tetrahydropyran represented by the formula (4) obtained in the second embodiment of the present invention, there may be mentioned 4-cyanotetrahydropyran, tetrahydropyran-4-carboxylic acid, methyl tetrahydropyran-4-carboxylate, ethyl tetrahydropyran-4-carboxylate, n-propyl tetrahydropyran-4-carboxylate, isopropyl tetrahydropyran-4-carboxylate, n-butyl tetrahydropyran-4-carboxylate, isobutyl tetrahydropyran-4-carboxylate, tert-butyl tetrahydropyran-4-carboxylate, cyclopropyl tetrahydropyran-4-carboxylate, benzyl tetrahydropyran-4-carboxylate, phenyl tetrahydropyran-4-carboxylate, etc.

Next, a process for preparing a 4-substituted tetrahydropyran which is the third embodiment of the present invention will be explained.

(A) Cyclization Reaction Step

The cyclization step of the present invention is a step of preparing a mixture of the 4-substituted tetrahydropyran-4-carboxylic acid ester and the 4-substituted tetrahydropyran-4-carboxylic acid by reacting a bis(2-halogenoethyl)ether and a 2-substituted acetic acid ester in the presence of a base in an organic solvent.

The bis(2-halogenoethyl)ether to be used in the cyclization step of the present invention is represented by the above-mentioned formula (5). In the formula (5), X is a halogen atom such as a fluorine atom, chlorine atom, bromine atom, iodine atom, etc.

As the specific examples of the bis(2-halogenoethyl)ether represented by the formula (5) to be used in the cyclization step of the present invention, there may be mentioned bis(2-fluoroethyl)ether, bis(2-chloroethyl)ether, bis(2-bromoethyl)ether, bis(2-iodoethyl)ether, etc.

The 2-substituted acetic acid ester to be used in the cyclization step of the present invention is shown by the above-mentioned formula (6). In the formula (6), R represents the above-mentioned groups, and $R^3$ represents a hydrocarbon group. As the above-mentioned hydrocarbon group, there may be mentioned, for example, a linear or branched alkyl group having 1 to 6 carbon atoms such as a methyl group, an ethyl group, a propyl group, a butyl group, a pentyl group, a hexyl group, etc.; a cycloalkyl group having 3 to 10 carbon atoms such as a cyclopropyl group, a cyclobutyl group, a cyclopentyl group, a cyclohexyl group, etc.; an aralkyl group in which a linear or branched alkyl group having 1 to 3 carbon atoms is bonded to an aryl group, such as a benzyl group, a phenethyl group, a phenylpropyl group, etc.; an aryl group having 6 to 20 carbon atoms such as a phenyl group, a tolyl group, a xylyl group, a mesityl group, a naphthyl group, etc., preferably an alkyl group, more preferably a methyl group or an ethyl group. Incidentally, these groups also contain various kinds of isomers.

As the specific examples of the 2-substituted acetic acid ester represented by the formula (6) to be used in the cyclization step of the present invention, there may be mentioned methyl cyanoacetate, ethyl cyanoacetate, n-propyl cyanoacetate, isopropyl cyanoacetate, n-butyl cyanoacetate, isobutyl cyanoacetate, tert-butyl cyanoacetate, cyclopropyl cyanoacetate, cyclobutyl cyanoacetate, cyclopentyl cyanoacetate, cyclohexyl cyanoacetate, benzyl cyanoacetate, phenyl cyanoacetate, dimethyl malonate, diethyl malonate, di-n-propyl malonate, diisopropyl malonate, di-n-butyl malonate, diisobutyl malonate, di-tert-butyl malonate, dicyclopropyl malonate, dibenzyl malonate, diphenyl malonate, etc.

An amount of the above-mentioned 2-substituted acetic acid ester to be used is preferably 1.0 to 20 mols, more preferably 2.0 to 4.0 mols based on 1 mol of the bis(2-halogenoethyl)ether.

As the base to be used in the cyclization step of the present invention, there may be mentioned, for example, an alkali metal hydride such as sodium hydride, potassium hydride, etc.; an alkali metal alkoxide such as sodium methoxide, sodium ethoxide, sodium isopropoxide, potassium t-butoxide, etc.; an alkali metal carbonate such as sodium carbonate, potassium carbonate, etc.; an alkali metal hydrogen carbonate such as sodium hydrogen carbonate, potassium hydrogen carbonate, etc.; an alkali metal hydroxide such as sodium hydroxide, potassium hydroxide, etc., preferably an alkali metal hydride, an alkali metal alkoxide, and/or an alkali metal carbonate is/are used. Incidentally, these bases may be used alone or in combination of two or more in admixture.

An amount of the above-mentioned base to be used is preferably 1.0 to 10.0 mols, more preferably 2.0 to 5.0 mols based on 1 mol of the bis(2-halogenoethyl)ether.

As the organic solvent to be used in the cyclization step of the present invention, it is not specifically limited so long as it does not inhibit the reaction, and there may be mentioned, for example, an amide such as N,N-dimethylformamide, N,N-dimethylacetamide, N-methyl-pyrrolidone, etc.; a urea such as N,N'-dimethylimidazolidinone, etc.; a sulfoxide such as dimethyl sulfoxide, sulfolane, etc.; a nitrile such as acetonitrile, propionitrile, etc.; an alcohol such as methanol, ethanol, n-butyl alcohol, isopropyl alcohol, n-butyl alcohol, t-butyl alcohol, etc.; an ether such as diisopropylether, dioxane, cyclopropylmethylether, etc.; an aromatic hydrocarbon such as benzene, toluene, xylene, etc.; a ketone such as acetone, methyl ethyl ketone, methyl isobutyl ketone, etc., preferably an amide or a sulfoxide is used. Incidentally, these organic solvents may be used alone or in combination of two or more in admixture.

An amount of the above-mentioned organic solvent to be used may be optionally adjusted depending on a degree of uniformity or condition of stirring of the reaction mixture, and is preferably 1 to 50 g, more preferably 2 to 20 g based on 1 g of the bis(2-halogenoethyl)ether.

The cyclization step of the present invention can be carried out by a method in which, for example, the bis(2-halogenoethyl)ether, the 2-substituted acetic acid ester, a base and an organic solvent are mixed, and stirred, etc. A reaction temperature at that time is preferably 20 to 150° C., more preferably 50 to 130° C., and a reaction pressure is not specifically limited.

According to the cyclization step of the present invention, a solution containing a mixture of the 4-substituted tetrahydropyran-4-carboxylic acid ester represented by the formula (7) and the 4-substituted tetrahydropyran-4-carboxylic acid represented by the formula (3) can be obtained, and in the present invention, the next step is usually carried out by using the solution as such or after concentration thereof. However, if necessary, the formed 4-substituted tetrahydropyran-4-carboxylic acid ester and the 4-substituted tetrahydropyran-4-carboxylic acid may be once separated and purified by the usual methods, for example, filtration, crystallization, recrystallization, distillation, column chromatography, etc., and then, the next step may be carried out.

Specific examples of the 4-substituted tetrahydropyran-4-carboxylic acid ester represented by the formula (7) obtained by the cyclization step of the present invention may be mentioned methyl 4-cyanotetrahydropyran-4-carboxylate, ethyl 4-cyanotetrahydropyran-4-carboxylate, n-propyl 4-cyanotetrahydropyran-4-carboxylate, isopropyl 4-cyanotetrahydropyran-4-carboxylate, n-butyl 4-cyanotetrahydropyran-4-carboxylate, isobutyl 4-cyanotetrahydropyran-4-carboxylate, tert-butyl 4-cyanotetrahydropyran-4-carboxylate, cyclopropyl 4-cyanotetrahydropyran-4-carboxylate, benzyl 4-cyanotetrahydropyran-4-carboxylate, phenyl 4-cyanotetrahydropyran-4-carboxylate, dimethyl tetrahydropyran-4,4-dicarboxylate, diethyl tetrahydropyran-4,4-dicarboxylate, di-n-propyl tetrahydropyran-4,4-dicarboxylate, diisopropyl tetrahydropyran-4,4-dicarboxylate, di-n-butyl tetrahydropyran-4,4-dicarboxylate, diisobutyl tetrahydropyran-4,4-dicarboxylate, di-tert-butyl tetrahydropyran-4,4-dicarboxylate, dicyclopropyl tetrahydropyran-4,4-dicarboxylate, dibenzyl tetrahydropyran-4,4-dicarboxylate, diphenyltetrahydropyran-4,4-dicarboxylate, etc. Also, specific examples of the 4-substituted tetrahydropyran-4-carboxylic acid represented by the formula (3) may include those as mentioned above.

(B) Hydrolysis Step

The hydrolysis step of the present invention is a step of preparing a 4-substituted tetrahydropyran-4-carboxylic acid represented by the formula (3) by subjecting a mixture of the 4-substituted tetrahydropyran-4-carboxylic acid ester represented by the formula (7) and the 4-substituted tetrahydropyran-4-carboxylic acid represented by the formula (3) to hydrolysis.

The hydrolysis step of the present invention is not specifically limited so long as it is a method which can hydrolyze a carboxylic acid ester, and preferably carried out in the presence of an acid or a base, water, water-soluble solvent or in a mixed solvent of water and a water-soluble solvent.

As the acid to be used in the hydrolysis step of the present invention, there may be mentioned, for example, a mineral acid such as hydrochloric acid, hydrobromic acid, hydroiodic acid, sulfuric acid, chlorosulfuric acid, nitric acid, etc.; an organic sulfonic acid such as methanesulfonic acid, ethanesulfonic acid, benzenesulfonic acid, p-toluenesulfonic acid, etc.; a halogenated carboxylic acid such as chloroacetic acid, dichloroacetic acid, etc., preferably a mineral acid, an organic sulfonic acid, more preferably a mineral acid is used. Incidentally, these acids may be used alone or in combination of two or more in admixture.

An amount of the above-mentioned acid to be used is preferably 0.01 to 10 mols, more preferably 2.0 to 5.0 mols based on 1 mol of the mixture of the 4-substituted tetrahydropyran-4-carboxylic acid ester and the 4-substituted tetrahydropyran-4-carboxylic acid.

As the base to be used in the hydrolysis step of the present invention, there may be mentioned, for example, an alkali metal hydroxide such as sodium hydroxide, potassium hydroxide, etc.; an alkali metal carbonate such as sodium carbonate, potassium carbonate, etc.; an alkali metal hydrogen carbonate such as sodium hydrogen carbonate, potassium hydrogen carbonate, etc.; an alkali metal alkoxide such as sodium methoxide, potassium methoxide, etc., preferably an alkali metal hydroxide, an alkali metal carbonate, more preferably an alkali metal hydroxide is used. Incidentally, these bases may be used alone or in combination of two or more in admixture.

An amount of the above-mentioned base to be used is preferably 0.01 to 10 mols, more preferably 2.0 to 5.0 mols based on 1 mol of the mixture of the 4-substituted tetrahydropyran-4-carboxylic acid ester and the 4-substituted tetrahydropyran-4-carboxylic acid.

As the above-mentioned mixed solvent of the water-soluble solvent or water and the water-soluble solvent, there may be used, for example, preferably an alcohol or a mixed solvent of water and an alcohol.

An amount of the above-mentioned water to be used is preferably 0.01 to 20 g, more preferably 0.1 to 10 g based on 1 g of the mixture of the 4-substituted tetrahydropyran-4-carboxylic acid ester and the 4-substituted tetrahydropyran-4-carboxylic acid.

As the above-mentioned alcohol, there may be mentioned, for example, methanol, ethanol, n-propyl alcohol, isopropyl alcohol, n-butyl alcohol, sec-butyl alcohol, t-butyl alcohol, pentyl alcohol, methoxyethanol, ethoxy-ethanol, ethylene glycol, triethylene glycol, etc., preferably methanol, ethanol, n-propyl alcohol, isopropyl alcohol, more preferably methanol, ethanol or isopropyl alcohol is used. Incidentally, these alcohols may be used alone or in combination of two or more in admixture, and may contain water.

An amount of the above-mentioned alcohol to be used is preferably 0.01 to 20 g, more preferably 0.1 to 10 g based on 1 g of the mixture of the 4-substituted tetrahydropyran-4-carboxylic acid ester and the 4-substituted tetrahydropyran-4-carboxylic acid.

The hydrolysis step of the present invention can be carried out by a method in which, for example, a mixture of the 4-substituted tetrahydropyran-4-carboxylic acid ester and the 4-substituted tetrahydropyran-4-carboxylic acid, an acid or a base, and a water-soluble solvent are mixed, and stirred, etc. A reaction temperature at that time is preferably −30 to 80° C., more preferably −10 to 40° C., and a reaction pressure is not specifically limited.

According to the hydrolysis step of the present invention, the 4-substituted tetrahydropyran-4-carboxylic acid can be obtained, and in the present invention, the next step may be carried out by once carrying out separation and purification after completion of the reaction by a usual method, for example, filtration, concentration, crystallization, recrystallization, distillation, column chromatography, etc., but the resulting material may be used as such in the next step without carrying out isolation and purification, or may be used after replacing the solvent to a solvent to be used in the next step.

(C) Decarboxylation Step

The decarboxylation step of the present invention is a step of preparing the 4-substituted tetrahydropyran represented by the formula (4) by subjecting the 4-substituted tetrahydropyran-4-carboxylic acid represented by the formula (3) to decarboxylation in the presence of a metal catalyst, and it may be carried out by the same method as in the decarboxylation of the above-mentioned first and the second embodiments. Specific examples of the 4-substituted tetrahydropyran-4-carboxylic acid represented by the formula (4) may include those as mentioned above.

Next, the preparation method of the 4-aminomethyltetrahydropyran and an acid salt thereof represented by the formula (9) in the fourth embodiment of the present invention is explained. The preparation process of the 4-aminomethyltetrahydropyran and an acid salt thereof is a reduction of 4-cyanotetrahydropyran represented by the formula (8) in which R is a cyano group in the above-mentioned formula (4) with hydrogen.

The Raney nickel to be used in the reduction of the present invention is an alloy comprising nickel and aluminum as main components, and that preferably with a nickel content of 10 to 90% by weight, more preferably 40 to 80% by weight is used. In general, developed Raney nickel is used, and a pretreated Raney nickel or a stabilized Raney nickel, which had been subjected to according to the various methods, may be also used. Further, that in which a metal such as cobalt, iron, lead, chromium, titanium, molybdenum, vanadium, manganese, tin, tungsten, etc. is/are contained in a Raney nickel may be also used.

An amount of the above-mentioned Raney nickel to be used is preferably 0.01 to 1.0 g, more preferably 0.05 to 0.5 g in terms of a nickel atom based on 1 g of the 4-cyanotetrahydropyran.

A concentration of the ammonia in the solvent containing ammonia to be used in the reaction of the present invention is preferably 0.1 to 50% by weight, more preferably 1 to 35% by weight.

As the solvent to be used in the reaction of the present invention, it is not specifically limited so long as it does not inhibit the reaction, and there may be mentioned, for example, water; an alcohol such as methanol, ethanol, n-propyl alcohol, isopropyl alcohol, n-butyl alcohol, sec-butyl alcohol, t-butyl alcohol, etc.; an aromatic hydrocarbon such as benzene, toluene, xylene, mesitylene, etc.; a halogenated aliphatic hydrocarbon such as chloroform, dichloroethane, etc.; an ether such as diethyl ether, tetrahydrofuran, diisopropylether, etc., preferably water, an alcohol, more preferably water, methanol, ethanol or isopropyl alcohol is used. Incidentally, these organic solvents may be used alone or in combination of two or more in admixture.

An amount of the above-mentioned solvent to be used may be optionally adjusted depending on a degree of uniformity or condition of stirring of the reaction mixture, and is preferably 0.1 to 100 ml, more preferably 1.0 to 10 ml based on 1 g of the 4-cyanotetrahydropyran.

An amount of the hydrogen to be usd in the reaction of the present invention is preferably 0.1 to 20 mols, more preferably 0.2 to 10 mols based on 1 mol of the 4-cyanotetrahydropyran.

The reaction of the present invention can be carried out, for example, by a method that a solvent containing 4-cyanotetrahydropyran, Raney nickel and ammonia is mixed, and reacted with hydrogen under stirring, etc. A reaction temperature at this time is preferably 0 to 150° C., more preferably 5 to 120° C., particularly preferably 5 to 80° C., and a reaction pressure is preferably 0.1 to 10 MPa, more preferably 0.1 to 1 MPa. Incidentally, after completion of the reaction, an appropriate acid is reacted with the 4-aminomethyltetrahydropyran to prepare an acid salt of the 4-aminomethyltetrahydropyran. As the above-mentioned acid salt to be used in the present invention, there may be mentioned a salt of an inorganic acid such as hydrogen chloride, hydrogen bromide, hydrogen iodide, hydrogen fluoride, sulfuric acid, hydrogen nitrate, etc., a salt of an organic acid such as formic acid, acetic acid, propionic acid, oxalic acid, succinic acid, maleic acid, salicylic acid, methanesulfonic acid, ethanesulfonic acid, trifluoromethanesulfonic acid, benzenesulfonic acid, p-toluenesulfonic acid, p-chlorobenzenesulfonic acid, p-bromobenzenesulfonic acid, phthalic acid, isophthalic acid, benzoic acid, etc.

Incidentally, 4-aminomethyltetrahydropyran which is a final product represented by the formula (9) and an acid salt thereof may be isolated and purified by, for example, after completion of the reaction, a general method such as filtration, concentration, distillation, recrystallization, colunm chromatography, etc. Also, after completion of the reaction, it is desired to carry out a post-treatment of the reaction mixture by using an amine such as triethylamine, tetraethylenepentamine, pentaethylene hexamine, etc. By using these amines, there are merits that, for example, solidification of the liquid in a reactor due to aggregation of Raney nickel can be prevented during distillation of the 4-aminomethyltetrahydropyran, a free 4-aminomethyltetrahydropyran can be prepared by removing carbon dioxide from a by-produced carbonic acid salt of the 4-aminomethyltetrahydropyran, and, contamination of ammonia in the 4-aminomethyltetrahydropyran can be prevented.

EXAMPLES

Next, the present invention will be explained in more detail by referring to Examples, but the scope of the present invention is not limited by these examples.

Example 1

Synthesis of Acetonitrile

In a flask made of glass equipped with a stirring device, a thermometer and a reflux condenser and having an inner volume of 50 ml were charged 200 mg (1.40 mmol) of copper(I) oxide, 25 ml of dimethyl sulfoxide and 5.0 g (55.8 mmol) of cyanoacetic acid with a purity of 95%, and under nitrogen atmosphere, the mixture was reacted at 110 to 120° C. for 30 minutes with stirring. After completion of the reaction, the reaction mixture was cooled to room temperature, and when the reaction mixture was analyzed by gas chromatography (Internal standard method), 2.17 g (Reaction yield: 95.0%) of acetonitrile was found to be formed.

Example 2

Synthesis of Acetonitrile

The reaction was carried out in the same manner as in Example 1 except for changing the solvent to N,N-dimethylformamide in Example 1. As a result, 2.25 g (Reaction yield: 98.3%) of acetonitrile was found to be formed.

Example 3

Synthesis of Acetonitrile

The reaction was carried out in the same manner as in Example 2 except for changing copper(I) oxide to 91 mg (1.40 mmol) of zinc powder and changing the reaction time to 3 hours in Example 2. As a result, 2.13 g (Reaction yield: 93.1%) of acetonitrile was found to be formed.

Example 4

Synthesis of Acetonitrile

The reaction was carried out in the same manner as in Example 2 except for changing copper(I) oxide to 226 mg (1.40 mmol) of iron(III) chloride and changing the reaction time to 5 hours in Example 2. As a result, 2.12 g (Reaction yield: 92.7%) of acetonitrile was found to be formed.

Example 5

Synthesis of Acetonitrile

The reaction was carried out in the same manner as in Example 2 except for changing copper(I) oxide to 125 mg (0.025 g was used based on 1 g of the cyanoacetic acid) of Raney nickel, and changing the reaction time to 3 hours in Example 2. As a result, 2.06 g (Reaction yield: 89.8%) of acetonitrile was found to be formed.

Example 6

Synthesis of Acetic Acid

In a flask made of glass equipped with a stirring device, a thermometer and a reflux condenser and having an inner volume of SO ml were charged 170 mg (1.19 mmol) of copper(I) oxide, 25 ml of dimethyl sulfoxide and 5.0 g (47.6 mmol) of malonic acid with purity of 99%, under nitrogen atmosphere, and the mixture was reacted at 110 to 120° C. for 1.5 hours under stirring. After completion of the reaction, the reaction mixture was cooled to room temperature, and when the reaction mixture was analyzed by gas chromatography (Internal standard method), 2.86 g (Reaction yield: 100%) of acetic acid was found to be formed.

Example 7

Synthesis of Acetic Acid

The reaction was carried out in the same manner as in Example 6 except for changing a solvent to N,N-dimethylformamide in Example 6. As a result, 2.86 g (Reaction yield: 100%) of acetic acid was found to be formed.

Example 8

Synthesis of 4-cyanotetrahydropyran

In a flask made of glass equipped with a stirring device, a thermometer, a dropping funnel and a reflux condenser and having an inner volume of 2 L were charged, under nitrogen atmosphere, 4.6 g (31.9 mmol) of copper(I) oxide and 200 g of pyridine, and a temperature of the mixture was raised to 100° C. under stirring. Then, a solution of 200 g (1.28 mol) of the 4-cyanotetrahydropyran-4-carboxylic acid with purity of 99% dissolved in 400 g of pyridine was gradually added dropwise to the above mixture while a temperature of the reaction mixture is maintained to 100 to 110° C., and the mixture was reacted at 100 to 110° C. for 1 hour. After completion of the reaction, the reaction mixture was cooled to room temperature, and 500 ml of water, 650 ml (7.80 mol) of conc. hydrochloric acid and 500 ml of toluene were successively added in this order to the mixture under stirring. After separating the aqueous layer and the organic layer (the toluene layer), the aqueous layer was extracted three times with each 500 ml of toluene, then, the said organic layer and these toluene extracts were combined and the mixture was concentrated under reduced pressure. The obtained concentrate was distilled under reduced pressure (100 to 120° C., 2.0 to 2.7 kPa) to give 133.5 g (Isolation yield: 93%) of 4-cyanotetrahydropyran with purity of 99% (areal percentage according to gas chromatography) as colorless liquid.

Physical properties of the 4-cyanotetrahydropyran are as follows.

CI-MS (m/e); 112 (M+1)

$^1$H-NMR (CDCl$_3$, δ (ppm)); 1.63 to 1.74 (2H, m), 1.80 to 1.89 (2H, m), 3.04 to 3.11 (1H, m), 3.43 to 3.50 (2H, m), 3.67 to 3.75 (2H, m)

Example 9

Synthesis of 4-cyanotetrahydropyran

In a flask made of glass equipped with a stirring device, a thermometer and a reflux condenser and having an inner volume of 30 ml were charged, under nitrogen atmosphere, 2.0 g (12.76 mmol) of 4-cyanotetrahydropyran-4-carboxylic acid with purity of 98%, 46 mg (0.319 mmol) of copper(I) oxide and 6.0 ml of N,N-dimethylformamide, and the mixture was reacted at 110 to 120° C. for 1 hour under stirring. After completion of the reaction, the reaction mixture was cooled to room temperature and analyzed by gas chromatography (Internal standard method), 1.41 g (Reaction yield: 100%) of 4-cyanotetrahydropyran was found to be formed.

Examples 10 to 38

Synthesis of 4-cyanotetrahydropyran

In the same manner as in Example 9 except for changing the catalyst, the solvent and/or the reaction time, the reaction was carried out as in Example 9. The results are shown in Table 1.

TABLE 1

| Example | Catalyst | Solvent$^{c)}$ | Reaction time (h) | Reaction yield (%) |
|---|---|---|---|---|
| 10 | Copper(I) oxide | Triethylamine | 0.5 | 98 |
| 11 | Copper(I) oxide | Tributylamine | 0.5 | 98 |
| 12 | Copper(I) oxide | N-methylpyrrolidone | 0.5 | 96 |
| 13 | Copper(I) oxide | N,N-dimethylacetamide | 0.5 | 100 |
| 14 | Copper(I) oxide | N,N'-dimethylimidazolidinone | 0.5 | 100 |
| 15 | Copper(I) oxide | Dimethyl sulfoxide | 0.5 | 98 |
| 16 | Copper(I) oxide | 2-Picoline | 1 | 98 |
| 17 | Copper(I) oxide | Quinoline | 1 | 100 |
| 18 | Copper(I) oxide | n-Butyl alcohol | 1 | 84 |
| 19 | Copper(I) oxide | Cyclopropyl methyl ether | 3 | 92 |
| 20 | Copper(I) oxide | Toluene/triethylamine(=5/1) | 1.5 | 99 |
| 21 | Copper(I) oxide | Toluene/N,N-dimethylformamide(=5/1) | 1.5 | 98 |
| 22 | Copper(I) oxide | Toluene/N,N-dimethylacetamide(=5/1) | 1.5 | 100 |
| 23 | Copper(I) oxide | Toluene/dimethyl sulfoxide(=5/1) | 1.5 | 100 |
| 24 | Copper(I) oxide | Water/N,N-dimethylformamide(=1/1) | 1.5 | 93 |
| 25 | Copper(I) oxide | Ethyl acetate/N,N-dimethylformamide(=1/5) | 1.5 | 100 |
| 26 | Copper(I) oxide | Ethyl acetate/N,N-dimethylacetamide(=1/5) | 1.5 | 100 |
| 27 | Copper(I) oxide | Ethyl acetate/dimethyl sulfoxide(=1/5) | 1.5 | 100 |
| 28 | Copper(I) oxide | Butyl acetate/N,N-dimethylformamide(=5/1) | 1.5 | 100 |
| 29 | Copper(I) oxide | Butyl acetate/N,N-dimethylacetamide(=5/1) | 1.5 | 100 |
| 30 | Copper(I) oxide | Butyl acetate/dimethyl sulfoxide(=3/2) | 1.5 | 100 |

TABLE 1-continued

| Example | Catalyst | Solvent[c] | Reaction time (h) | Reaction yield (%) |
|---|---|---|---|---|
| 31 | Copper powder | Pyridine | 5 | 90 |
| 32 | Copper powder | N,N-dimethylformamide | 5 | 95 |
| 33 | Iron[a] | N,N-dimethylformamide | 5 | 97 |
| 34 | Iron(III) chloride | N,N-dimethylformamide | 5 | 96 |
| 35 | Nickel(II) acetylacetonate[b] | Pyridine | 1.5 | 97 |
| 36 | Raney nickel[b] | N,N-dimethylformamide | 5 | 83 |
| 37 | Zinc powder | N,N-dimethylformamide | 3 | 100 |
| 38 | Zinc chloride | N,N-dimethylformamide | 5 | 100 |

[a] 0.1 mol was used based on 1 mol of 4-cyanotetrahydropyran-4-carboxylic acid.
[b] 0.025 g was used based on 1 g of 4-cyanotetrahydropyran-4-carboxylic acid.
[c] In the parentheses are a volume ratio of these solvents.

Example 39

Synthesis of Tetrahydropyran-4-carboxylic Acid

In a flask made of glass equipped with a stirring device, a thermometer and a reflux condenser and having an inner volume of 50 ml were charged 1.0 g (5.74 mmol) of tetrahydropyran-4,4-dicarboxylic acid with purity of 100%, 21 mg (0.14 mmol) of copper(I) oxide and 3.0 ml of pyridine under nitrogen atmosphere, and the mixture was reacted at 110 to 120° C. for 1 hour under stirring. After completion of the reaction, the reaction mixture was cooled to room temperature, 5 ml of water, 5 ml (60 mmol) of conc. hydrochloric acid and 10 ml of ethyl acetate were successively added in this order to the reaction mixture. The aqueous layer and the organic layer (the ethyl acetate layer) were separated, the aqueous layer was extracted three times with each 10 ml of ethyl acetate, then, the organic layer and the ethyl acetate extracts were combined and the mixture was concentrated under reduced pressure to give 534 mg (Isolation yield: 72%) of tetrahydropyran-4-carboxylic acid with purity of 100% (analytical value by differential refractometry) as white crystals.

Physical properties of the tetrahydropyran-4-carboxylic acid are as follows.

Melting point; 83 to 84° C.

CI-MS (m/e); 131 (M+1)

$^1$H-NMR (DMSO-$d_6$, δ (ppm)); 1.45 to 1.60 (2H, m), 1.68 to 1.76 (2H, m), 2.40 to 2.52 (1H, m), 3.28 to 3.37 (2H, m), 3.77 to 3.83 (2H, m), 12.19 (1H, brs)

Example 40

Synthesis of Tetrahydropyran-4-carboxylic Acid

In a flask made of glass equipped with a stirring device, a thermometer and a reflux condenser and having an inner volume of 50 ml were charged, under nitrogen atmosphere, 1.0 g (5.74 mmol) of tetrahydropyran-4,4-dicarboxylic acid, 32 mg (0.57 mmol) of iron and 3.0 ml of pyridine, and the mixture was reacted at 110 to 120° C. for 1 hour under stirring. After completion of the reaction, the reaction mixture was cooled to room temperature, and 5 ml of water, 5 ml (60 mmol) of conc. hydrochloric acid and 10 ml of ethyl acetate were successively added in this order to the reaction mixture. The aqueous layer and the organic layer (the ethyl acetate layer) were separated, and the aqueous layer was washed three times with each 10 ml of ethyl acetate. Then, the organic layer and the ethyl acetate extracts were combined and concentrated under reduced pressure to give 548 mg (Isolation yield: 73%) of tetrahydropyran-4-carboxylic acid with purity of 100% (analytical value by differential refractometry) as white crystals.

Example 41

Synthesis of 4-cyanotetrahydropyran

In a flask made of glass equipped with a stirring device, a thermometer and a dropping funnel and having an inner volume of 10 L were charged, under argon atmosphere, 4.72 L of N,N-dimethylformamide and 1486 g (27.5 mol) of sodium methoxide, an inner temperature was cooled to 0° C., then 2753 g (27.5 mol) of cyanomethyl acetate with purity of 99% was gradually added dropwise to the above mixture under stirring. After completion of the dropwise addition, the mixture was stirred at room temperature for 3 hours to prepare a solution containing a sodium salt of cyanomethyl acetate.

In a flask made of glass equipped with a stirring device, a thermometer, a reflux condenser and a dropping funnel and having an inner volume of 20 L was charged 1589 g (11.0 mol) of bis(2-chloroethyl)ether with purity of 99%, and after raising a temperature of the mixture to 64° C., the above-mentioned solution containing the sodium salt of cyanomethyl acetate was gradually added dropwise thereto. After completion of the dropwise addition, the mixture was subjected to cyclization under nitrogen atmosphere at 80° C. for 9 hours.

After completion of the reaction, the reaction mixture was cooled to 0° C., and 1760 g (22.0 mol) of a 50% sodium hydroxide aqueous solution was gradually added dropwise thereto. After completion of the dropwise addition, the mixture was subjected to hydrolysis at room temperature for 1 hour. After completion of the reaction, the reaction mixture was cooled to 0° C., and 2.21 L (26.5 mol) of 35% hydrochloric acid was gradually added dropwise thereto. After completion of the dropwise addition, the mixture was stirred at room temperature for 30 minutes.

Then, 4.72 L of toluene was added to the reaction mixture, the mixture was azeotropically dehydrated at 50° C. under reduced pressure (4.67 kPa). Thereafter, toluene was added so that an amount of the toluene remained in the reaction mixture was made 4.72 L, and then, the mixture was heated to 50° C. and filtered. The filtrated material was washed with 3.15 L of toluene, and the washed solution was combined with the filtrate to obtain an organic solution containing 4-cyanotetrahydropyran-4-carboxylic acid.

In a flask made of glass equipped with a stirring device, Dean-Stark device, a thermometer and a dropping funnel and having an inner volume of 20 L were charged the organic solution containing the above-mentioned 4-cyanotetrahydropyran-4-carboxylic acid, 1.57 L of toluene and 39.5 g (275 mmol) of copper(I) oxide, and decarboxylation was carried out under argon atmosphere at 115° C. for 1.5 hours while removing low-boiling point compounds.

After completion of the reaction, the reaction mixture was cooled to room temperature, and filtered, and the filtrated material was washed with 1.57 L of toluene. Also, to the filtrate were added 1.57 L of water and 64 ml of 35% hydrochloric acid to make a pH of the reaction mixture 1.8, then, the aqueous layer was separated and extracted with 3.15 L of toluene. The above-mentioned filtrate and the extract were combined, and concentrated at 60° C. under reduced pressure (10.67 kPa). To the concentrate was added 2650 ml of ethyl acetate, the mixture was washed with 660 ml of a saturated sodium chloride aqueous solution, and the organic layer was concentrated. The concentrate was distilled under reduced pressure (120° C., 1.33 kPa) to give 529.3 g (Isolation yield: 42.9%) of 4-cyanotetrahydropyran with purity of 99% (areal percentage according to gas chromatography).

Example 42

Synthesis of Tetrahydropyran-4-carboxylic Acid

In a flask made of glass equipped with a stirring device, a thermometer and a dropping funnel and having an inner volume of 200 ml were charged, under nitrogen atmosphere, 115.6 ml of N,N-dimethylformamide and 13.51 g (0.25 mol) of sodium methoxide, an inner temperature was cooled to 5° C., then 33.02 g (0.25 mol) of dimethyl malonate was gradually added dropwise thereto under stirring. After completion of the dropwise addition, the mixture was stirred at room temperature for 3 hours to prepare a solution containing a sodium salt of dimethyl malonate.

In a flask made of glass equipped with a stirring device, a thermometer, a reflux condenser and a dropping funnel and having an inner volume of 200 ml was charged 14.45 g (0.10 mol) of bis(2-chloroethyl)ether with purity of 99%, and after raising a temperature of the mixture to 80° C., the above-mentioned solution containing the sodium salt of dimethyl malonate was gradually added dropwise thereto. After completion of the dropwise addition, the mixture was subjected to cyclization under nitrogen atmosphere at 85° C. for 20 hours.

After completion of the reaction, the reaction mixture was filtered, and the filtrated material was washed with 30 ml of N,N-dimethylformamide. The filtrate and the washed solution were combined, the temperature of the mixture was cooled to 5° C., and 36.0 g (0.45 mol) of a 50% sodium hydroxide aqueous solution was gradually added dropwise thereto. After completion of the dropwise addition, 52 ml of water was added to the mixture, and the resulting mixture was subjected to hydrolysis at room temperature for 3 hours. After completion of the reaction, the reaction mixture was cooled to 5° C., 44 ml (0.45 mol) of 35% hydrochloric acid was gradually added dropwise thereto. After completion of the dropwise addition, the mixture was stirred at room temperature for 30 minutes, and then, the reaction mixture was concentrated under reduced pressure. To the concentrate were added 200 ml of ethyl acetate and 100 ml of water and the resulting mixture was separated, then, the obtained organic layer was washed with 20 ml of a saturated aqueous sodium chloride solution and concentrated under reduced pressure. To the obtained concentrate was added 30 ml of methyl isobutyl ketone, and the mixture was filtered to give crystals of tetrahydropyran-4,4-dicarboxylic acid.

In a flask made of glass equipped with a stirring device, a thermometer and a dropping funnel and having an inner volume of 50 ml were charged the above-mentioned tetrahydropyran-4,4-dicarboxylic acid, 17.6 ml of pyridine and 123.1 mg (0.86 mmol) of copper(I) oxide, and the mixture was subjected to decarboxylation under nitrogen atmosphere at 110 to 120 C. for 1 hour. After completion of the reaction, the mixture was cooled to room temperature, 30 ml of water, 30 ml (360 mmol) of conc. hydrochloric acid and 60 ml of ethyl acetate were successively added in this order, and the aqueous layer and the organic layer were separated. After the aqueous layer was washed three times with each 60 ml of ethyl acetate, these extracts and the organic layer were combined and concentrated under reduced pressure to give 3.15 g (Isolation yield: 24.2%) of tetrahydropyran-4-carboxylic acid with purity of 100% (analytical value by differential refractometry) as white crystals.

Example 43

Synthesis of 4-aminomethyltetrahydropyran

In an autoclave made of stainless equipped with a stirring device, a thermometer and a pressure gauge and having an inner volume of 200 ml were charged 10.0 g (90.0 mmol) of 4-cyanotetrahydropyran, 50.0 g of 22% by weight ammonia-methanol solution and 2.0 g (17.0 mmol in terms of a nickel atom) of developed Raney nickel (available from Nikki Chemical Co., Ltd.; sponge nickel N154D), and the mixture was reacted under hydrogen atmosphere (0.51 to 0.61 MPa) at 45 to 55° C. for 17 hours under stirring. After completion of the reaction, insoluble materials were filtered, and the filtrated material was washed with 30 ml of methanol. The filtrate and the washed solution were combined and concentrated under reduced pressure, and then, the concentrate was distilled under reduced pressure (73 to 74° C., 2.67 kPa) to tive 7.94 g (Isolation yield; 76.6%) of 4-aminomethyltetrahydropyran as colorless liquid.

Physical properties of the 4-aminomethyltetrahydropyran are as follows.

$^1$H-NMR (DMSO-$d_6$, δ (ppm)); 1.02 to 1.16 (2H, m), 1.10 to 1.50 (2H, brs), 1.34 to 1.45 (1H, m), 1.56 to 1.61 (2H, m), 2.39 (2H, d, J=6.3 Hz), 3.20 to 3.29 (2H, m), 3.81 to 3.86 (2H, m)

CI-MS (m/e); 116 (M+1), 99

Example 44

Synthesis of 4-aminomethyltetrahydropyran Hydrochloride

In an autoclave made of stainless equipped with a stirring device, a thermometer and a pressure gauge and having an inner volume of 25 L were charged 1685.8 g (containing 15.2 mol of 4-cyanotetrahydropyran) of 65.9% by weight 4-cyanotetrahydropyran-toluene solution, 8.8 kg of 5.86% by weight ammonia-methanol solution, 337.2 g (2.86 mmol in terms of a nickel atom) of developed Raney nickel (available from Nikki Chemical Co., Ltd.; sponge nickel N154D) and 2.1 L of methanol, and the mixture was reacted under hydrogen atmosphere (0.51 to 0.61 MPa) at 50 to 60° C. for 7 hours under stirring. After completion of the reaction, insoluble materials were filtered, the filtrated material was washed with 2.0 L of methanol, and the filt-rate and the washed solution were combined and concentrated under reduced pressure.

To a reaction vessel made of glass equipped with a stirring device and a thermometer and having an inner volume of 3 L were charged said concentrate and 833 ml of tetraethylenepentamine, the mixture was stirred at 105 to 115° C. for 2 hours. After completion of the stirring, said solution was distilled under reduced pressure (70 to 80° C., 1.73 to 4.67 kPa) to obtain 1430.2 g of the distilled solution containing 4-aminomethyltetrahydropyran.

To a reaction vessel made of glass equipped with a stirring device, a thermometer and a dropping funnel and having an inner volume of 20 L were charged 8.3 L of n-butanol and 1232 ml (15.0 mol) of 37% by weight hydrochloric acid, and in a salt-ice bath, said distulled solution was gradually added dropwise to the mixture while maintaining a temperature of the mixture to 0° C. or thereabround, and after completion of dropwise addition, the mixture was stirred at room temperature for 30 minutes. An operation that the resulting solution was concentrated under reduced pressure, and 5.0 L of n-butanol was added to the concentrate and further concentrated was repeated twice. Then, in a salt-ice bath, when the concentrate was stirred for 50 minutes, a solid was precipitated and filtered. The filtered material was washed with 1.7 L of toluene, and then, it was dried under reduced pressure at 60° C. to give 1692.9 g (Isolation yield: 73.6%) of 4-aminomethyltetrahydropyran hydrochloride as white crystals.

Physical properties of 4-aminomethyltetrahydropyran hydrochloride are as follows.

Melting point; 190 to 193° C.

$^1$H-NMR (DMSO-$d_6$, δ (ppm)); 1.13 to 1.26 (2H, m), 1.63 to 1.68 (2H, m), 1.78 to 1.92 (1H, m), 2.67 (2H, d, J=7.1 Hz), 3.22 to 3.30 (2H, m), 3.82 to 3.87 (2H, m), 8.21 (3H, brs)

CI-MS (m/e); 116 (M+1-HCl), 99

Example 45

Synthesis of 4-aminomethyltetrahydropyran

In an autoclave made of stainless equipped with a stirring device, a thermometer and a pressure gauge and having an inner volume of 200 ml were charged 10.0 g (90.0 mmol) of 4-cyanotetrahydropyran, 100 ml of 22% by weight ammonia methanol solution and 2.0 g (17.0 mmol in terms of a nickel atom) of developed Raney nickel (available from Nikki Chemical Co., Ltd.; sponge nickel N154D), and the mixture was reacted under hydrogen atmosphere (0.51 to 0.61MPa) at 50 to 60° C. for 5 hours under stirring. After completion of the reaction, insoluble materials were filtered, the filtered material was washed with 30 ml of methanol, and the filtrate and the washed solution were combined. When this solution was analyzed by gas chromatography (Internal standard method), 8.84 g (Reaction yield: 85.3%) of 4-aminomethyltetrahydropyran was found to be formed. Incidentally, bis(4-tetrahydropyranylmethyl)amine which is a by-product was not formed.

Comparative Example 1

Synthesis of 4-aminomethyltetrahydropyran

In an autoclave made of stainless equipped with a stirring device, a thermometer and a pressure gauge and having an inner volume of 200 ml were charged 10.0 g (90.0 mmol) of 4-cyanotetrahydropyran, 100 ml of methanol and 2.0 g (17.0 mmol in terms of a nickel atom) of developed Raney nickel (available from Nikki Chemical Co., Ltd.; sponge nickel N154D), and the mixture was reacted under hydrogen atmosphere (0.51 to 0.61 MPa) at 50 to 60° C. for 5 hours under stirring. After completion of the reaction, insoluble materials were filtered, the filtered material was washed with 30 ml of methanol, and the filtrate and the washed solution were combined. When this solution was analyzed by gas chromatography (Internal standard method), 7.19 g (Reaction yield: 52.7%) of the 4-aminomethyltetrahydropyran was found to be formed. Incidentally, 4.28 g of bis(4-tetrahydropyranylmethyl)amine which is a by-product was formed.

Utilizable Field in Industry

According to the present invention, an industrially suitable process for preparing a nitrile compound or a carboxylic acid compound or a 4-substituted tetrahydropyran can be provided which can prepare a nitrile compound or a carboxylic acid compound or a 4-substituted tetrahydropyran from an acetic acid compound or a 4-substituted tetrahydropyran-4-carboxylic acid with high yield under mild conditions with a simple and easy process.

Also, according to the present invention, an industrially suitable process for preparing a 4-substituted tetrahydropyran which can prepare a 4-substituted tetrahydropyran with high yield from a bis(2-halogenoethyl)ether and a 2-substituted acetic acid ester can be provided under mild conditions with a simple and easy process.

The nitrile compound or the carboxylic acid compound or the 4-substituted tetrahydropyran obtaind by the the present invention is a useful compound as a starting material or a synthetic intermediate for medicine, agricultural chemicals, etc.

Moreover, according to the present invention, an industrially suitable process for preparing a 4-aminomethyltetrahydropyran and an acid salt thereof which can prepare a 4-aminomethyltetrahydropyran and an acid salt thereof from a 4-cyanotetrahydropyran with high yield can be provided.

The 4-aminomethyltetrahydropyran and an acid salt thereof obtained by the present invention is a useful compound as a starting material or a synthetic intermediate for medicine, agricultural chemicals, etc.

The invention claimed is:

1. A process for preparing a 4-substituted tetrahydropyran represented by the formula (4):

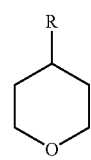

wherein R represents a cyano group, a carboxyl group or an ester group, which comprises subjecting a 4-substituted tetrahydropyran-4-carboxylic acid represented by the formula (3):

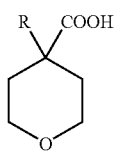

(3)

wherein R has the same meaning as defined above, to decarboxylation in the presence of a metal catalyst.

2. The process for preparing a 4-substituted tetrahydropyran according to claim 1, wherein the metal catalyst is a catalyst containing at least one metal selected from the group consisting of copper, iron, nickel and zinc.

3. The process for preparing a 4-substituted tetrahydropyran according to claim 2, wherein the decarboxylation is carried out in a solvent.

4. The process for preparing a 4-substituted tetrahydropyran according to claim 3, wherein the solvent is a tertiary amine, a pyridine, an amide, a sulfoxide, or a mixed solvent of any one of the above solvents and an aromatic hydrocarbon or an acetic acid ester.

5. The process for preparing a 4-substituted tetrahydropyran according to claim 1, wherein a temperature of the decarboxylation is 50 to 150° C.

* * * * *